United States Patent [19]

Ohno et al.

[11] 4,334,067
[45] Jun. 8, 1982

[54] FLAVAN COMPOUNDS AND ACID ADDITION SALTS THEREOF

[75] Inventors: Sachio Ohno; Mitsuaki Nagasaka, both of Aichi; Kazuo Kato, Nagoya, all of Japan

[73] Assignee: Maruko Seiyaku Co., Ltd., Aichi, Japan

[21] Appl. No.: 201,877

[22] Filed: Oct. 29, 1980

[30] Foreign Application Priority Data

Oct. 29, 1979 [JP] Japan .................................. 54-139685
Nov. 7, 1979 [JP] Japan .................................. 54-144194

[51] Int. Cl.³ .................. C07D 413/04; C07D 311/68
[52] U.S. Cl. ..................................... 544/151; 544/376; 546/196; 549/399
[58] Field of Search ................ 544/151, 376; 546/196; 260/345.2

[56] References Cited

U.S. PATENT DOCUMENTS 4,048,317  9/1977  Watts ................................. 260/345.2
4,119,643 10/1978  Watts ................................. 260/345.2

OTHER PUBLICATIONS

Fletcher et al., *Chem. Abstracts*, vol. 59, (1963), cols. 13923-13924.

*Primary Examiner*—Henry R. Jiles
*Assistant Examiner*—R. W. Ramsuer
*Attorney, Agent, or Firm*—Sughrue, Mion, Zinn, Macpeak & Seas

[57] ABSTRACT

A flavan compound represented by the formula (I)

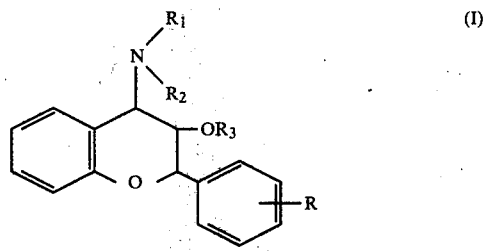

wherein R, $R_1$, $R_2$ and $R_3$ are as defined above, and the pharmaceutically acceptable acid addition salt thereof, which are useful as pharmaceutical agent having anti-convulsive, anti-ulcer, anti-arrythmic and diuretic activities.

8 Claims, No Drawings

FLAVAN COMPOUNDS AND ACID ADDITION SALTS THEREOF

BACKGROUND OF THE INVENTION

1. Field of the Invention

This invention relates to a flavan compound represented by the formula (I)

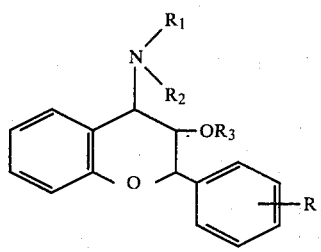

wherein R represents hydrogen or an alkoxy group, $R_1$ represents hydrogen or an alkyl group, $R_2$ represents an alkyl group, a hydroxyalkyl group or a substituted aminoalkyl group, or $R_1$ and $R_2$, when taken together with the nitrogen atom to which they are attached, can form a piperidino group, an N-substituted piperazino group or a morpholino group, and $R_3$ represents hydrogen or an acetyl group, which is useful as pharmaceutical agent having anti-convulsive, anti-ulcer, anti-arrythmic and diuretic activities.

2. Description of the Prior Art

As far as the present inventors know, there have been no prior art compounds having a closely related chemical structure to the compounds of the formula (I) above and having pharmacological activities similar to those of the present invention. The flavan compounds of the formula (I) are therefore novel type of pharmaceutical compounds.

DETAILED DESCRIPTION OF THE INVENTION

The present invention relates to novel flavan compounds represented by the formula (I)

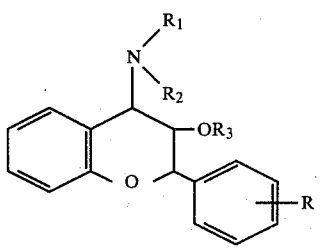

wherein R represents hydrogen or an alkoxy group, $R_1$ represents hydrogen or an alkyl group, $R_2$ represents an alkyl group, a hydroxyalkyl group or a substituted aminoalkyl group, or $R_1$ and $R_2$, when taken together with the nitrogen atom to which they are attached, can form a piperidino group, an N-substituted piperazino group or a morpholino group, and $R_3$ represents hydrogen or an acetyl group, and the acid addition salts thereof.

The term "alkyl" as used herein means a straight or branched alkyl group having 1 to 4 carbon atoms such as methyl, ethyl, n-propyl, isopropyl, n-butyl, sec-butyl or tert-butyl group. The "alkoxy" means a -O-($C_1$-$C_4$)alkyl.

The term "hydroxyalkyl" as used herein means a hydroxyalkyl group having 2 to 4 carbon atoms in the alkyl moiety thereof, for example, a hydroxyethyl or hydroxypropyl group.

The term "substituted aminoalkyl" as used herein means a dialkylaminoalkyl group having 2 to 4 carbon atoms in each alkyl group such as dimethylaminoethyl, diethylaminoethyl, dimethylaminopropyl, diethylaminopropyl and the like; or a piperidinoalkyl group or a morpholinoalkyl group, each having 2 to 4 carbon atoms in the alkyl moiety.

The term "N-substituted piperazino" as used herein means an N-($C_1$-$C_4$)alkylpiperazino group which may optionally be substituted with a hydroxy group on the alkyl moiety thereof, for example, a 4-methylpiperazino group, a 4-hydroxyethylpiperazino group and the like.

The term "acid addition salt" as used herein means acid addition salts formed with pharmaceutically acceptable inorganic or organic acids, for example, hydrochloride, sulfate, methanesulfonate, maleate, tartrate, citrate, lactate and the like.

The flavan compounds represented by the formula (I) above can exist in the 2,3-cis-3,4-trans or 2,3-trans-3,4-trans form represented by the following formulae:

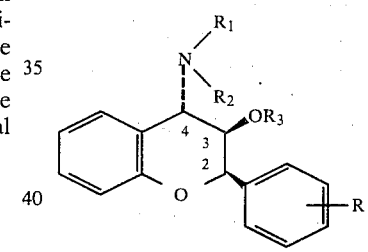

2,3-cis-3,4-trans form

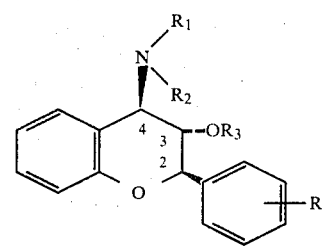

2,3-trans-3,4-trans form and the present invention includes within the scope thereof each of the above stereoisomers as well as a mixture thereof.

A preferred class of the flavan compounds of the present invention is those represented by the following formulae (Ia) and (Ib):

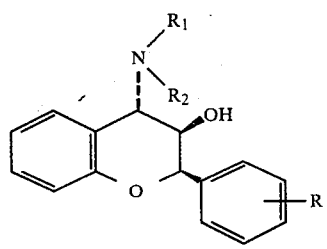

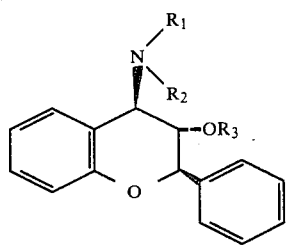

wherein R, $R_1$, $R_2$ and $R_3$ are as defined above.

Typical examples of the flavan compounds of the present invention which are most preferred in view of their pharmacological activities are:

2,3-cis-3,4-trans-4-(2-diethylaminoethylamino)-4'-methoxyflavan-3-ol and an acid addition salt thereof, 2,3-cis-3,4-trans-4'-methoxy-4-(4-methylpiperazin-1-yl)flavan-3-ol and an acid addition salt thereof, 2,3-cis-3,4-trans-4'-methoxy-4-(3-morpholinopropylamino)flavan-3-ol and an acid addition salt thereof, 2,3-cis-3,4-trans-4-(3-dimethylaminopropylamino)-4'-methoxyflavan-3-ol and an acid addition salt thereof, 2,3-trans-3,4-trans-4-piperidinoflavan-3-ol and an acid addition salt thereof, 2,3-trans-3,4-trans-4-piperidinoflavan-3-ol and an acid addition salt thereof, 2,3-trans-3,4-trans-4-(4-methylpiperazin-1-yl)-flavan-3-ol and an acid addition salt thereof, 2,3-trans-3,4-trans-3-acetoxy-4-(4-methylpiperazin-1-yl)flavan and an acid addition salt thereof, and 2,3-trans-3,4-trans-4-(2-dimethylaminoethylamino)-flavan-3-ol and an acid addition salt thereof.

The flavan compounds of the present invention represented by the formula (I) above wherein $R_3$ represents hydrogen can be easily prepared by reacting a corresponding 2,3-cis- or 2,3-trans-flav-3-en epoxide of the formula (II)

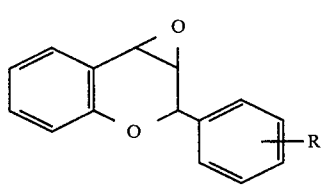

wherein R is as defined above, with an amine of the formula (III)

wherein $R_1$ and $R_2$ are as defined above, in the presence or absence of an inert organic solvent at a temperature of from about 60° C. to about 100° C., for a period of about 1 to 3 hours.

The amine of the formula (III) can be used at a proportion of at least an equimolar amount relative to the epoxide of the formula (II) and can be a large excess amount so as to serve also as a reaction solvent.

The invert organic solvent used in the reaction can be any type of solvents so long as they do not adversely affect the reaction as well as the desired product, and typical examples of solvents are benzene, toluene, xylene, tetrahydrofuran, etc.

The product thus obtained can be isolated from the reaction mixture by a conventional procedure, for example, evaporation of the solvent, addition of water to precipitate the product, extraction, filtration or a combination thereof.

The flavan compounds of the present invention represented by the formula (I) above wherein $R_3$ represents an acetyl group (i.e., 3-acetoxy compounds) can be easily prepared from the corresponding 3-hydroxy flavan compound obtained as described above by acetylation. The acetylation reaction can be conducted in a conventional manner, for example, by reacting the 3-hydroxyflavan compound with an acetylating agent such as acetic anhydride, acetyl chloride and the like, in an amount of at least an equimolar amount of the acetylating agent relative to the 3-hydroxyflavan compound in an organic solvent such as chloroform, carbon tetrachloride, pyridine, etc., at room temperature (about 15° to 30° C.) for a period of about 5 to about 16 hours. The 3-acetoxy compounds thus obtained can be isolated from the reaction mixture in the same manner as described for the isolation of the 3-hydroxyflavan compounds.

The acid addition salts of the thus obtained flavan compounds can easily be prepared in a conventional manner, for example, by reacting the flavan compound in the free form with a pharmaceutically acceptable acid in a solvent such as ethanol at an elevated temperature and isolating the acid addition salt by solvent extraction or precipitation.

The flavan compounds of the present invention exhibit excellent anti-convulsive, anti-ulcer, anti-arrythmic and diuretic activities in mammals and, therefore, are useful as anti-convulsive, anti-ulcer, anti-arrythmic and diuretic agents in mammals. These compounds can be administered orally or parenterally, e.g., intramuscularly or intravenously, to mammals in various conventional dosage forms.

The 2,3-cis-3,4-cis epoxide compounds of the formula (II) used as starting materials are novel compounds and can be easily prepared by the following reaction scheme:

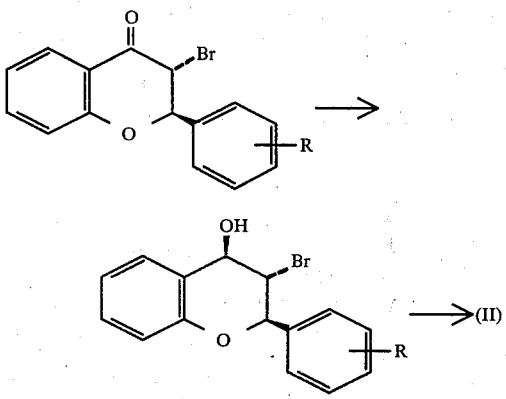

wherein R is as defined above.

That is, a 2,3-trans-3-bromoflavan compound (V) is reduced with a reducing agent such as lithium aluminum hydride to obtain a 2,3-trans-3,4-trans-3-bromo-4-hydroxyflavan of the formula (VI) which is then reacted with sodium hydride to obtain the desired 2,3-cis-3,4-cis epoxide. The 2,3-trans epoxide compounds of the formula (II) are known compounds.

The present invention is further illustrated in greater detail by the following Examples and Reference Examples, but these examples are given for illustrative purposes only and are not to be construed as limiting the present invention.

EXAMPLE 1

A mixture of 2.7 g of 2,3-cis-4'-methoxyflav-3-en epoxide and 12 ml of 2-diethylaminoethylamine was heated on a water bath for 3 hours. After allowing the mixture to cool, water was added thereto and the precipitated crystals were filtered and washed with water. Recrystallization of the product from a mixture of dichloromethane and petroleum ether yielded 3,4 g of 2,3-cis-3,4-trans-4-(2-diethylaminoethylamino)-4'-methoxyflavan-3-ol as colorless needles having a melting point of 102° C.

Elementary Analysis: Calcd. for $C_{22}H_{30}N_2O_3 = 370.496$ (Molecular Weight): C, 71.32; H, 8.16; N, 7.56 (%): Found: C, 71.18; H, 8.02; N, 7.55 (%).

Then, a mixture of 3,4 g of 2,3-cis-3,4-trans-4-(2-diethylaminoethylamino)-4'-methoxyflavan-3-ol obtained as above, 4 g of maleic acid and 30 ml of ethanol was warmed. After allowing the reaction mixture to cool, the precipitated crystals were filtered and recrystallized from a mixture of ethanol and diethyl ether to obtain 5.3 g of 2,3-cis-3,4-trans-4-(2-diethylaminoethylamino)-4'-methoxyflavan-3-ol dimaleate as colorless needles having a melting point of 152° C. (Compound A).

Elementary Analysis: Calcd. for $C_{22}H_{30}N_2O_3.2C_4H_4O_4 = 602.644$: C, 59.79; H, 6.36; N, 4.65 (%): Found: C, 59.83; H, 6.41; N, 4.53 (%).

EXAMPLE 2

A mixture of 3 g of 2,3-cis-4'-methoxyflav-3-en epoxide and 10 ml of piperidine was heated on a water bath for 3 hours. Thereafter, water was added to the reaction mixture and the resulting mixture was extracted with diethyl ether. The extract was washed with water and dried over anhydrous magnesium sulfate. The solvent was distilled off and the resulting oil was dissolved in 20 ml of ethanol. Hydrogen gas was bubbled through the solution, and the solution was warmed for a while, followed by allowing to cool. The precipitated crystals were separated by filtration and recrystallized from ethanol to obtain 4 g of 2,3-cis-3,4-trans-4'-methoxy-4-piperidinoflavan-3-ol hydrochloride as colorless needles having a melting point of 250° C. (with decomposition).

Elementary Analysis: Calcd. for $C_{21}H_{25}NO_3.HCl = 375.899$: C, 67.10; H, 6.97; N, 3.73 (%): Found: C, 67.01; H, 6.99; N, 3.81 (%).

EXAMPLE 3

A mixture of 3.1 g of 2,3-cis-4'-methoxyflav-3-en epoxide, 5 ml of N-methylpiperazine and 20 ml of benzene was heated while refluxing for 2 hours. Thereafter, the solvent was distilled off and water was added to the residue. The solidified substance was separated by filtration, washed with water and recrystallized from a mixture of dichloromethane and petroleum ether to obtain 2.6 g of 2,3-cis-3,4-trans-4'-methoxy-4-(4-methylpiperazin-1-yl)flavan-3-ol as colorless plates having a melting point of 142° C.

Elementary Analysis: Calcd. for $C_{21}H_{26}N_2O_3 = 354.453$: C, 71.16; H, 7.39; N, 7.90 (%): Found: C, 71.33; H, 7.45; N, 7.86 (%).

Then, 2,3-cis-3,4-trans-4'-methoxy-4-(4-methylpiperazin-1-yl)flavan-3-ol obtained as above and maleic acid were treated in the same manner as described in Example 1 and the resulting crystals were recrystallized from a mixture of ethanol and diethyl ether to obtain 2,3-cis-3,4-trans-4'-methoxy-4-(4-methylpiperazin-1-yl)flavan-3-ol dimaleate as colorless needles having a melting point of 174° C. (Compound B) in a quantitative yield.

Elementary Analysis: Calcd. for $C_{21}H_{26}N_2O_3.2C_4H_4O_4 = 586.601$: C, 59.38; H, 5.84; N, 4.78 (%): Found: C, 59.35; H, 5.80; N, 4.74 (%).

In the same manner as described in Examples 1 to 3, the following compounds were obtained.

EXAMPLE 4

2,3-cis-3,4-trans-4-[4-(2-hydroxyethyl)piperazin-1-yl]-4'-methoxyflavan-3-ol. Recrystallized from a mixture of ethanol and petroleum ether. Colorless prisms having a melting point of 174° C.

Elementary Analysis: Calcd. for $C_{22}H_{28}N_2O_4 = 384.479$: C, 68.73; H, 7.34; N, 7.29 (%): Found: C, 68.89; H, 7.31; N, 7.38 (%).

2,3-cis-3,4-trans-4-[4-(2-hydroxyethyl)piperazin-1yl]-4'-methoxyflavan-3-ol dimaleate. Recrystallized from a mixture of ethanol and diethyl ether. Colorless prisms having a melting point of 193° C.

Elementary Analysis: Calcd. for $C_{22}H_{28}N_2O_4.2C_4H_4O_4 = 616.628$: C, 58.44; H, 5.88; N, 4.54 (%): Found: C, 58.29; H, 5.73; N, 4.44 (%).

EXAMPLE 5

2,3-cis-3,4-trans-4'-methoxy-4-(3-morpholinopropylamino)flavan-3-ol. Recrystallized from a mixture of dichloromethane and petroleum ether. Colorless needles having a melting point of 114° C.

Elementary Analysis: Caldc. $C_{23}H_{30}N_2O_4 = 398.506$: C, 69.32; H, 7.59; N, 7.03 (%): Found: C, 69.28; H, 7.72; N, 7.15 (%).

2,3-cis-3,4-trans-4'-methoxy-4-(3-morpholinopropylamino)flavan-3-ol dimaleate (Compound C). Recrystallized from a mixture of ethanol and diethyl ether.

Colorless needles having a melting point of 165° C. (decomposition).

Elementary Analysis: Calcd. for $C_{23}H_{30}N_2O_4.2C_4H_4O_4=630.655$: C, 59.04; H, 6.07; N, 4.44 (%): Found: C, 59.16; H, 6.24; N, 4.57 (%).

EXAMPLE 6

2,3-cis-3,4-trans-4-(3-dimethylaminopropylamino)-4'-methoxyflavan-3-ol (Compound D). Recrystallized from a mixture of dichloromethane and n-hexane. Colorless needles having a melting point of 83° C.

Elementary Analysis: Calcd. for $C_{21}H_{28}N_2O_3=356.469$: C, 70.76; H, 7.92; N, 7.86 (%): Found: C, 70.87; H, 8.06; N, 7.65 (%).

EXAMPLE 7

2,3-cis-3,4-trans-4'-methoxy-4-morpholinoflavan-3-ol. Recrystallized from a mixture of dichloromethane and n-hexane. Colorless flakes having a melting point of 155° C.

Elementary Analysis: Calcd. for $C_{20}H_{23}NO_4=341.411$: C, 70,36; H, 6.79; N, 4.10 (%): Found: C, 70.54; H, 6.83; N, 4.02 (%).

2,3-cis-3,4-trans-4'-methoxy-4-morpholinoflavan-3-ol hydrochloride. Recrystallized from ethanol. Colorless needles having a melting point of 243° C.

Elementary Analysis: Calcd. for $C_{20}H_{23}NO_4.HCl=377.872$: C, 63.58; H, 6.40; N, 3.71 (%). Found: C, 63.42; H, 6.31; N, 3.66 (%).

EXAMPLE 8

2,3-cis-3,4-trans-4-n-butylamino-4'-methoxyflavan-3-ol. Recrystallized from a mixture of dichloromethane and petroleum ether. Colorless needles having a melting point of 115° C.

Elementary Analysis: Calcd. for $C_{20}H_{25}NO_3=327.427$: C, 73.37; H, 7.70; N, 4.28 (%): Found: C, 73.51; H, 7.82; N, 4.33 (%).

2,3-cis-3,4-trans-4-n-butylamino-4'-methoxyflavan-3-ol hydrochloride. Recrystallized from a mixture of ethanol and diethyl ether. Colorless needles having a melting point of 219° C.

Elementary Analysis: Calcd. for $C_{20}H_{25}NO_3.HCl=363.888$: C, 66.02; H, 7.20; N, 3.85 (%): Found: C, 66.20; H, 7.22; N, 3.84 (%).

EXAMPLE 9

2,3-cis-3,4-trans-4-(3-hydroxypropylamino)-4'-methoxyflavan-3-ol. Recrystallized from a mixture of chloroform and petroleum ether. Colorless needles having a melting point of 131° C.

Elementary Analysis: Calcd. for $C_{19}H_{23}NO_4=329.399$: C, 69.28; H, 7.04; N, 4.25 (%): Found: C, 69.48; H, 7.19; N, 4.09 (%).

2,3-cis-3,4-trans-4-(3-hydroxypropylamino)-4'-methoxyflavan-3-ol maleate. Recrystallized from a mixture of ethanol and diethyl ether. Colorless needles having a melting point of 143° C.

Elementary Analysis: Calcd. for $C_{19}H_{23}NO_4.C_4H_4O_4=445.474$: C, 62.01; H, 6.11; N, 3.14 (%): Found: C, 62.17; H, 6.10; N, 3.10 (%).

EXAMPLE 10

4 g of 2,3-trans-falv-3-en epoxide and 10 ml of morpholine were added to 20 ml of benzene and the mixture was heated under refluxing for 3 hours. Thereafter, the solvent was distilled off and water was added to the residue. The solidified substance was separated by filtration, washed with water and recrystallized from a mixture of chloroform and n-pentane to obtain 4.8 g of 2,3-trans-3,4-trans-4-morpholinoflavan-3-ol as colorless needles having a melting point of 206° C.

Elementary Analysis: Calcd. for $C_{19}H_{21}NO_3=311.384$: C, 73.29; H, 6.80; N, 4.50 (%): Found: C, 73.44; H, 6.97; N, 4.46 (%).

EXAMPLE 11

A mixture of 1.5 g of 2,3-trans-flav-3-en epoxide and 15 ml of piperidine was heated on a water bath for 2 hours. After allowing the reaction mixture to cool, the mixture was extracted with diethyl ether. The extract was washed with water and dried over magnesium sulfate. The solvent was distilled off and the resulting oily substance was crystallized from petroleum ether. The crystals thus obtained was separated by filtration and recrystallized from a mixture of diethyl ether and n-pentane to obtain 2 g of 2,3-trans-3,4-trans-4-piperidinoflavan-3-ol as colorless needles having a melting point of 142° C.

Elementary Analysis: Calcd. for $C_{20}H_{23}NO_2=309.412$: C, 77.64; H, 7.49; N, 4.53 (%): Found: C, 77.83; H, 7.52; N, 4.55 (%).

Then, a mixture of 2 g of 2,3-trans-3,4-trans-4-piperidinoflvan-3-ol obtained as above, 2 g of maleic acid and 15 ml of ethanol was warmed. After allowing the mixture to cool, the precipitated crystals were separated by filtration and recrystallized from a mixture of methanol and diethyl ether to obtain 2.5 g of 2,3-trans-3,4-trans-4-piperidinoflavan-3-ol maleate as colorless needles having a melting point of 189° C. (with decomposition) (Compound E).

Elementary Analysis: Calcd. for $C_{20}H_{23}NO_2.C_4H_4O_4=425.486$: C, 67.75; H, 6.40; N, 3.29 (%): Found: C, 67.79; H, 6.34; N, 3.33 (%).

EXAMPLE 12

2.1 g of 2,3-trans-3,4-trans-4-piperidinoflavan-3-ol was dissolved in 10 ml of pyridine and 5 ml of acetic anhydride was added to the solution, followed by allowing the mixture to stand overnight. Thereafter, water was added to the reaction mixture, and the precipitated crystals were separated by filtration, washed with water and recrystallized from a mixture of dichloromethane and n-pentane to obtained 1.8 g of 2,3-trans-3,4-trans-3-acetoxy-4-piperidinoflavan as colorless needles having a melting point of 143° C.

Elementary Analysis: Calcd. for $C_{22}H_{25}NO_3=351.449$: C, 75.19; H, 7.17; N, 3.99 (%): Found: C, 75.00; H, 7.23; N, 3.80 (%).

EXAMPLE 13

A mixture of 3.1 g of 2,3-trans-flav-3-en epoxide and 20 ml of N-methylpiperazine was heated on a water bath for 2 hours. After allowing the reaction mixture to cool, water was added thereto and the precipitated crystals were separated by filtration and washed with water. Recrystallization of the product from a mixture of chloroform and petroleum ether yielded 4.4 g of 2,3-trans-3,4-trans-4-(4-methylpiperazin-1-yl)flavan-3-ol as colorless needles having a melting point of 236° C.

Elementary Analysis: Calcd. for $C_{20}H_{24}N_2O_2=324.426$: C, 74.05; H, 7.46; N, 8.63 (%): Found: C, 74.21; H, 7.38; N, 8.61 (%).

Then, 2,3-trans-3,4-trans-4-(4-methylpiperazin-1-yl)-flavan-3-ol obtained as above and maleic acid were treated in the same manner as described in Example 11 and the resulting crystals were recrystallized from a mixture of ethanol and diethyl ether to obtain 2,3-trans-3,4-trans-4-(4-methylpiperazin-1-yl)flavan-3-ol dimaleate (Compound F) as colorless needles having a melting point of 198° C. (decomposition) in a quantitative yield.

Elementary Analysis: Calcd. for $C_{20}H_{24}N_2O_2.2C_4H_4O_4 = 556.575$: C, 60.43; H, 5.80; N, 5.03 (%): Found: C, 60.38; H, 5.77; N, 4.92 (%).

EXAMPLE 14

2 g of 2,3-trans-3,4-trans-4-(4-methylpiperazin-1-yl)flavan-3-ol was dissolved in 20 ml of chloroform. 10 ml of pyridine and 5 ml of acetic anhydride were added to the solution and the mixture was stirred for 8 hours at room temperature. The solvent was then distilled off, and water added to the resulting residue, followed by allowing to stand. The solidified product was separated by filtration, washed with water and recrystallized from a mixture of dichloromethane and n-pentane to obtain 1.5 g of 2,3-trans-3,4-trans-3-acetoxy-4-(4-methylpiperazin-1-yl)flavan as colorless needles having a melting point of 178° C.

Elementary Analysis: Calcd. for $C_{22}H_{26}N_2O_3 = 366.464$: C, 72.11; H, 7.15; N, 7.65 (%): Found: C, 71.92; H, 6.99; N, 7.54 (%).

Then, 2,3-trans-3,4-trans-3-acetoxy-4-(4-methylpiperazin-1-yl)flavan obtained as above and maleic acid were treated in the same manner as described in Example 11, and the resulting crystals were recrystallized from a mixture of methanol and diethyl ether to obtain 2,3-trans-3,4-trans-3-acetoxy-4-(4-methylpiperazin-1-yl)flavan dimaleate (Compound G) as colorless flakes having a melting point of 209° C. in a quantitative yield.

Elementary Analysis: Calcd. for $C_{22}H_{26}N_2O_3.2C_4H_4O_4 = 598.612$: C, 60.20; H, 5.73; N, 4.68 (%): Found: C, 60.31; H, 5.84; N, 4.51 (%).

EXAMPLE 15

2,3-trans-flav-3-en epoxide and 1-hydroxyethylpiperazine were treated in the same manner as described in Example 13 to obtain the following compounds:

2,3-trans-3,4-trans-4-[4-(2-hydroxyethyl)piperazin-1-yl]flavan-3-ol. Recrystallized from a mixture of chloroform and n-pentane. Colorless prisms having a melting point of 194° C.

Elementary Analysis: Calcd. for $C_{21}H_{26}N_2O_3 = 354.453$: C, 71.16; H, 7.39; N, 7.90 (%): Found: C, 71.31; H, 7.53; N, 7.76 (%).

2,3-trans-3,4-trans-4-[4-(2-hydroxyethyl)piperazin-1-yl]flavan-3-ol dimaleate. Recrystallized from a mixture of ethanol and diethyl ether. Colorless needles having a melting point of 168° C. (decomposition).

Elementary Analysis: Calcd. for $C_{21}H_{26}N_2O_3.2C_4H_4O_4 = 586.601$: C, 59.38; H, 5.84; N, 4.78 (%): Found: C, 59.44; H, 5.83; N, 4.71 (%).

EXAMPLE 16

2,3-trans-flav-3-en epoxide and 2-dimethylaminoethylamine were treated in the same manner as described in Example 11 to obtain the following compounds:

2,3-trans-3,4-trans-4-(2-dimethylaminoethylamino)flavan-3-ol. Recrystallized from a mixture of dichloromethane and n-pentane. Colorless prisms having a melting point of 82° C.

Elementary Analysis: Calcd. for $C_{19}H_{24}N_2O_2 = 312,415$: C, 73.05; H, 7.74; N, 8.97 (%): Found: C, 73.11; H, 7.79; N, 9.02 (%).

2,3-trans-3,4-trans-4-(2-dimethylaminoethylamino)flavan-3-ol dimaleate (Compound H). Recrystallized from a mixture of ethanol and diethyl ether. Colorless needles having a melting point of 175° C.

Elementary Analysis: Calcd. for $C_{19}H_{24}N_2O_2.2C_4H_4O_4 = 544.563$: C, 59.55; H, 5.92; N, 5.14 (%): Found: C, 59.33; H, 5.99; N, 5.07 (%).

EXAMPLE 17

2,3-Trans-flav-3-en epoxide and 3-morpholinopropylamine were treated in the same manner as described in Example 11 to obtain the following compounds:

2,3-trans-3,4-trans-4-(3-morpholinopropylamino)flavan-3-ol. Recrystallized from a mixture of dichloromethane and petroleum ether. Colorless needles having a melting point of 142° C.

Elementary Analysis: Calcd. for $C_{22}H_{28}N_2O_3 = 368.480$: C, 71.71; H, 7.66; N, 7.60 (%): Found: C, 71.85; H, 7.75; N, 7.58 (%).

2,3-trans-3,4-trans-4-(3-morpholinopropylamino)flavan-3-ol dimaleate. Recrystallized from a mixture of ethanol and diethyl ether. Colorless needles having a melting point of 190° C. (decomposition).

Elementary Analysis: Calcd. for $C_{22}H_{28}N_2O_3.2C_4H_4O_4 = 600.628$: C, 59.99; H, 6.04; N, 4.66 (%): Found: C, 59.87; H, 6.09; N, 4.52 (%).

Preparation of Starting Material 38 g of 2,3-trans-3-bromo-4'-methoxyflavanone was added slowly to a mixture of 2.8 g of lithium aluminum hydride and 160 ml of tetrahydrofuran while cooling with ice and stirring. After 1 hour, the reaction mixture was poured into ice-water which had been rendered acidic with hydrochloric acid and the precipitated crystals were separated by filtration. The crystals were washed successively with water and ethanol and recrystallized from a mixture of acetone and n-hexane to obtain 32 g of 2,3-trans-3,4-trans-3-bromo-4'-methoxyflavan-4-ol as colorless needles having a melting point of 199° C. (decomposition).

Elementary Analysis: Calcd. for $C_{16}H_{15}O_3Br = 335.200$: C, 57.33; H, 4.51 (%): Found: C, 57.43; H, 4.58 (%).

Then, 2.7 g of 50% sodium hydride was added slowly to a mixture of 15.4 g of 2,3-trans-3,4-trans-3-bromo-4'-methoxyflavan-4-ol obtained as above and 110 ml of tetrahydrofuran while cooling with ice. After 30 minutes, the reaction mixture was poured into ice-water and the precipitated crystals were separated by filtration. The crystals were washed with water and recrystallized from a mixture of dichloromethane and n-hexane to obtain 10.9 g of 2,3-cis-3,4-cis-4'-methoxyflav-3-en epoxide as colorless prisms having a melting point of 100° C.

Elementary Analysis: Calcd. for $C_{16}H_{14}O_3 = 254.288$: C, 75.57; H, 5.55 (%): Found: C, 75.39; H, 5.62 (%).

The pharmacological activities and the acute toxicity of the flavan compounds of the present invention having the formula (I) are described below.

Anti-convulsive Activity

The test compound was administered intraperitoneally to ddY male mice (weighing 20 to 25 g, 7 mice per group), and, 15 minutes thereafter, pulse (A.C. 100 V, 200 msec.) was applied to the mice from a corneal electrode, and the duration time of tonic flexor, tonic extensor and clonic convulsion were determined.

As a result, Compounds A, B, C and E (described in previous Examples) administered at a dose of 60 mg/kg were found to have an anti-convulsive activity comparable to that of Phenytoin (5,5-diphenyl-2,4-imidazolidinedione) administered at a dose of 40 mg/kg.

Anti-arrhythmic Activity

An aqueous solution of aconitine was injected continuously at a rate of 3 μg/kg/minute to Wistar male rats (weighing 220 to 270 g, five rats per group) through a polyethylene cannula inserted into the femoral vein. The test compounds were administered 10 minutes before the administration of aconitine.

The cardiac arrhythmia was determined by electrocardiographic recording of II lead on the limbs and the generation of descending large QRS complex was taken as the ventricular extrasystole and the observation was conducted until ventricular fibrillation was produced.

As a result, it was found that Compounds B and H (described in previous Examples) apparently exhibited at a dose of 10 mg/kg an activity for prolonging the time required for producing the cardiac arrhythmia superior to Ajmaline [(17R)-Ajmalan-17,21α-diol] administered at a dose of 5 mg/kg.

Diuretic Activity

Wistar male rats (weighing 200 to 250 g, 9 rats per group) fasted 18 hours before the test but freely received drinking water were used. A 0.9% (by weight) physiological saline solution containing the test compound was orally charged through a stomach tube in an amount of 3 ml/100 g of body weight. Immediately thereafter, the rats were placed in a stainless steel cage and the urine was collected during a period of 5 hours after the administration and the urine volume was measured.

The results obtained are shown in Table 1 below.

TABLE 1

| Test Compounds | Dose (mg/kg) | Number of Rats | Volume Ratio of Urine |
|---|---|---|---|
| Control | | 9 | 1.0 |
| Compound C | 100 | 9 | 2.1 |
| Compound E | 100 | 9 | 2.8 |
| Compound F | 100 | 9 | 2.2 |
| Compound G | 50 | 9 | 3.0 |

As is apparent from the above Table, the compounds of this invention increased the urine volume to at least two times the urine volume collected from the non-mediated control rat group.

Anti-Ulcerous Activity (Restraint Water-Immersion Stress Ulcer)

BALB/C type male mice weighing about 20 g which fasted for 17 hours before the test were placed in a poly(vinyl chloride) cyclindrical restraint cage having an inside diameter of 35 mm and the mice were immersed in water at 15° C. to the level of xiphisternum of mice for a period of 5 hours. Immediately thereafter, stomach was extracted and 1 ml of 0.5% (by weight) formalin solution was injected into the stomach. After fixing for about 10 minutes, the stomach was incised along the greater curvature thereof and the ulcer generated was obserbed by a stereoscopic microcope. The results obtained are shown in Table 2 below.

TABLE 2

| Test Compound | Dose (mg/kg) | Number of Mice | Ulcerous Index (mm) | % Inhibition (%) |
|---|---|---|---|---|
| Control | | 8 | 54.4 | |
| Compound G | 10 | 8 | 37.6 | 30.8 |
| Compound G | 50 | 8 | 14.3 | 73.7 |
| Atropine Sulfate | 10 | 8 | 30.7 | 43.8 |

As is apparent from the above results, the compound of this invention inhibited significantly the stress ulcer as compared with control and atropine sulfate.

Acute Toxicity

The test compounds were administered intraperitoneally or orally to ddY male mice (weighing 20 to 25 g, 16 mice per group). After observing general conditions of mice for 7 days after administration, 50% lethal dose [$LD_{50}$ (mg/kg)] was determined. The results obtained are shown in Table 3 below.

TABLE 3

| Test Compounds | $LD_{50}$ (mg/kg) i.v. | p.o. |
|---|---|---|
| Compound A | 1,000 | 2,000 |
| Compound B | 1,000 | 2,000 |
| Compound C | 500 | 1,500 |
| Compound D | 1,000 | 1,500 |
| Compound E | 1,000 | 1,500 |
| Compound F | 300 | 300 |
| Compound G | 300 | 1,000 |
| Compound H | 300 | 300 |

What is claimed is:

1. A flavan compound represented by the formula (I)

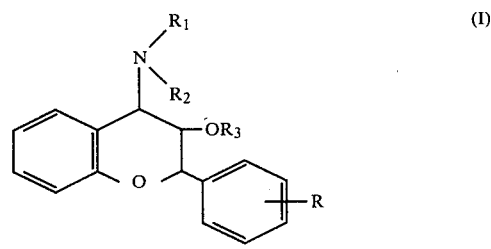

wherein R represents hydrogen or an alkoxy group, $R_1$ represents hydrogen or an alkyl group, $R_2$ represents an alkyl group, a hydroxyalkyl group or a substituted aminoalkyl group, or $R_1$ and $R_2$, when taken together with the nitrogen atom to which they are attached, can form a piperidino group, an N-substituted piperazino group or a morpholino group, and $R_3$ represents hydrogen or an acetyl group, with the proviso that when R is hydrogen, $R_2$ is a substituted aminoalkyl group, and the pharmaceutically acceptable acid addition salts thereof.

2. The flavan compound according to claim 1 represented by the formula (Ia)

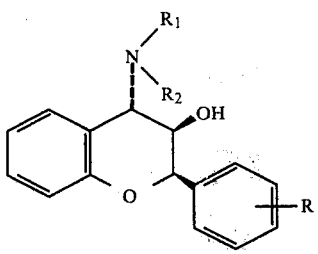

(Ia)

wherein R represents hydrogen or an alkoxy group, $R_1$ represents hydrogen or an alkyl group, $R_2$ represents an alkyl group, a hydroxyalkyl group or a substituted aminoalkyl group, or $R_1$ and $R_2$, when taken together with the nitrogen atom to which they are attached, can form a piperidino group, an N-substituted piperazino group or a morpholino group, with the proviso when R is hydrogen, $R_2$ is a substituted aminoalkyl group, and the pharmaceutically acceptable acid addition salts thereof.

3. The flavan compound according to claim 1 represented by the formula (Ib)

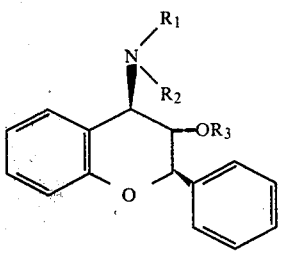

(Ib)

wherein $R_1$ represents hydrogen or an alkyl group, $R_2$ represents a substituted aminoalkyl group, and $R_3$ represents hydrogen or an acetyl group, and the pharmaceutically acceptable acid addition salts thereof.

4. 2,3-Cis-3,4-trans-4-(2-diethylaminoethylamino)-4'-methoxyflavan-3-ol and an acid addition salt thereof, according to claim 1.

5. 2,3-Cis-3,4-Trans-4'-methoxy-4-(4-methylpiperazin-1-yl)flavan-3-ol and an acid addition salt thereof, according to claim 1.

6. 2,3-Cis-3,4-trans-4'-methoxy-4-(3-morpholinopropylamino)flavan-3-ol and an acid addition salt thereof, according to claim 1.

7. 2,3-Cis-3,4-trans-4-(3-dimethylaminopropylamino)-4'-methoxyflavan-3-ol and an acid addition salt thereof, according to claim 1.

8. 2,3-Trans-3,4-trans-4-(2-dimethylaminoethylamino)-flavan-3-ol and an acid addition salt thereof, according to claim 1.

* * * * *